(12) United States Patent
Lin

(10) Patent No.: US 8,968,792 B2
(45) Date of Patent: Mar. 3, 2015

(54) PHARMACEUTICAL COMBINATION FOR THE TREATMENT OF RENAL FAILURE IN PETS

(71) Applicant: Cheng Yi Lin, Taoyuan (TW)

(72) Inventor: Cheng Yi Lin, Taoyuan (TW)

(*) Notice: Subject to any disclaimer, the term of this patent is extended or adjusted under 35 U.S.C. 154(b) by 64 days.

(21) Appl. No.: 13/803,843

(22) Filed: Mar. 14, 2013

(65) Prior Publication Data

US 2013/0266667 A1    Oct. 10, 2013

(30) Foreign Application Priority Data

Mar. 23, 2012 (TW) .............................. 101109979 A

(51) Int. Cl.
| | |
|---|---|
| *A61K 33/00* | (2006.01) |
| *A61K 31/7004* | (2006.01) |
| *A61K 31/19* | (2006.01) |
| *A61M 1/28* | (2006.01) |
| *A61K 33/20* | (2006.01) |
| *A61K 33/06* | (2006.01) |
| *A61K 9/00* | (2006.01) |
| *A61K 9/08* | (2006.01) |

(52) U.S. Cl.
CPC .............. *A61K 33/20* (2013.01); *A61K 31/7004* (2013.01); *A61K 33/06* (2013.01); *A61K 33/00* (2013.01); *A61K 31/19* (2013.01); *A61K 9/0019* (2013.01); *A61K 9/08* (2013.01)
USPC .............. 424/600; 514/54; 514/577; 210/646

(58) Field of Classification Search
USPC ...................... 424/600; 514/54, 577; 210/646
See application file for complete search history.

(56) References Cited

U.S. PATENT DOCUMENTS

| | | | | |
|---|---|---|---|---|
| 6,380,163 | B1 * | 4/2002 | Martis et al. ................. | 514/15.4 |
| 2006/0016752 | A1 * | 1/2006 | Hai et al. ....................... | 210/647 |
| 2008/0085325 | A1 * | 4/2008 | Carlsson et al. .............. | 424/601 |

OTHER PUBLICATIONS

Bersenas, "A clinical reveiw of peritoneal dialysis", Journal of Veterinary Emergency and Critical Care, pp. 605-617, (2011).*
Lin Kai-Wei, "Prognostic Indicators Affecting the Outcome of Acute Renal Failure in Small Animals and Evaluation of Related Infection by Using Central Venous Catheter in Dogs," Veterinary Medicine Institute of National Chung-Hsing University, master thesis, 2007.

* cited by examiner

*Primary Examiner* — Ernst V Arnold
*Assistant Examiner* — Kyung Sook Chang
(74) *Attorney, Agent, or Firm* — Bacon & Thomas, PLLC

(57) ABSTRACT

The present invention relates to a pharmaceutical combination for the treatment of renal failure in pets, caused by various diseases or ineffective to traditional renal therapy or renal replacement therapy thereby incapable of restoring health. The pharmaceutical combination of the present invention is administered by subcutaneous injection to pets in need thereof, with various advantages including simple use, no requirement for surgery, hospitalization and/or fluid infusion, faster recovery of health status, reduced medical costs, significantly improved recovery rate, reduced mortality and the likes. The pharmaceutical combination of the present invention can also be used for the continuous care treatment of pets with renal failure.

6 Claims, 3 Drawing Sheets

PHARMACEUTICAL COMBINATION FOR THE TREATMENT OF RENAL FAILURE IN PETS

CROSS-REFERENCED APPLICATION

This application claims priority from Taiwan patent application number 101109979 filed on Mar. 23, 2012, incorporated herein by reference in its entirety.

TECHNICAL FIELD

The invention relates to the pharmaceutical combination for the treatment of renal failure caused by various diseases in pets.

BACKGROUND

Renal failure is one of the common diseases in human or animals. Diagnosis of renal failure means that more than 75% of kidney loses normally physiological functions, leading to retention of metabolic toxins, disturbance of body fluids, electrolytes and pH, and even to serious systemic complications causing death. Lin (Lin Kai-Wei, "*Prognostic Indicators Affecting the Outcome of Acute Renal Failure in Small Animals and Evaluation of Related Infection by Using Central Venous Catheter in Dogs*", Veterinary Medicine Institute of National Chung-Hsing University, master thesis, 2007) reports that renal damage caused by acute renal failure (ARF) is reversible, however the mortality rates of ARF following different treatments (for example, traditional infusion therapy, peritoneal dialysis therapy and hemodialysis therapy) still remain between 30-83%. (Behrend E N, Grauer G F, Mani I, Groman R P, Salman M D, Greco D S, "*Hospital-acquired acute renal failure in dogs: 29 cases*" (1983-1992), *J Am Vet Med Assoc* 208: 537-541, 1996; Crisp M S, Chew D J, DiBartola S P, Birchard S J, "*Peritoneal dialysis in dogs and cats: 27cases*" (1976-1987), *J Am Vet Med Assoc* 195: 1262-1266, 1989; Forrester S D, McMillan N S, Ward D L, "*Retrospective evaluation of acute renal failure in dogs*", *J Vet Intern Med* 16: 354, 2002.) Also, Lin reports that in the period of from January of 2000 to December of 2006, 1339 dogs and 241 cats received medical treatments due to renal failure in Veterinary Teaching Hospital of National Chung-Hsing University, and the yearly prevalence rate and mortality rate of renal failure are respectively 4-10% and 49-59% in dogs, and 2-10% and 33-62% in cats. In animals determined as suffering acute renal failure (including 501 dogs and 69 cats), the overall yearly morality rate is 81.2% in dogs and 65.2% in cats.

Due to high morality rate of ARF in small animals, the prognostic indications associated with ARF have been intensively investigated to act as early prognostic indication and in turns for selection of appropriate treatment. The prognosis of ARF depends on the cause, severity of renal injury, and accompanying diseases, however literature data in this context are still limited and the results reported are not always consistent.

Current renal failure treatments in small animals include traditional therapy, renal replacement therapy, and diet therapy. Traditional therapy and renal replacement therapy are further described.

1. Transitional Therapy

Traditional therapy for renal failure in small animals mainly includes supportive therapy and infusion therapy (namely, vascular fluid infusion), in combination with medication if necessary, for the correction of body fluids, electrolytes and pH, and reduction of advanced renal damage. Traditional therapy for renal failure are mainly focused on the treatment of reversible renal failure where kidney is temporarily injured or the kidney index is temporarily increased due to other factors and can be resumed after treatment. Irreversible renal failure generally progresses to more severe conditions leading to kidney diseases and even to death. If the kidney index such as BUN (blood urea nitrogen) and CRE (creatinine) becomes worse, the veterinarian will announce euthanasia or advise peritoneal dialysis or hemodialysis therapy, however sometimes the pet still can not recover from renal failure and even die after peritoneal dialysis and hemodialysis therapy.

2. Renal Replacement Therapy

Renal replacement therapy refers to the treatment of temporary substitution for kidney functions in order to restore normal kidney functions, including peritoneal dialysis, hemodialysis, and even kidney transplants and the likes. ARF is one of indications of peritoneal dialysis or hemodialysis in dogs and cats. Traditionally, the response from supportive therapy (i.e., vascular fluid infusion) for 3 to 4 weeks is a criterion to determine whether the pet can recover from renal failure. Specifically, if a pet's health can not be restored from renal failure after supportive therapy and/or fluid infusion therapy, the pet will be requested for dialysis therapy. The pet with renal failure may survive for additional several months via intervention of dialysis therapy. When animals suffer severe oligouria or even anuria, and traditional therapies (supportive therapy and/or fluid infusion therapy) are ineffective to improve azotemia and correct body fluids, electrolytes and pH, a dialysis therapy (peritoneal dialysis or hemodialysis) must be conducted immediately. (Cowgill L D, Elliott D A. Hemodialysis. In: DiBartola S P, ed. "*Fluid Therapy in Small Animal Practice*", 2th ed. W.B. Saunder Co., Philadelphia, USA, 1615-1633, 2000; Whittemore J C, Webb C B. "*Beyond Fluid Therapy: Treating Acute Renal Failure*", *CompCont Ed Pract Vet*, 27: 288-297, 2005) Hemodialysis is technically feasible in the treatment of severe uremia, however it is not very common in consideration of availability and economy (about 160,000 NT dollars per week, with uncertain results in the continuous treatment). Peritoneal dialysis and hemodialysis will be described respectively.

A. Peritoneal Dialysis (PD)

Principle and Method:

Peritoneal dialysis is the method of implanting a permanent dialysis catheter into body for direct infusion of a dialysis solution containing electrolytes and glucose in an approximate physiological concentration into abdominal cavity, thereby small molecules (such as uremia waste) and ions in plasma can be exchanged with the dialysis solution through peritoneum acting as dialysis film by diffusion, convention or microfiltration, to correct disturbed electrolytes and body fluids.

Contraindications and Indications:

Peritoneal dialysis is mainly dependent on peritoneum as a dialysis film for substance exchange, thus any conditions which impede the exchange of dialysis solution will retard the feasibility of peritoneal dialysis, for example abdominal wall damage or peritoneal infection leading to the loss of the peritoneal exchange area of more than 50%. The contraindications of peritoneal dialysis in animals may include severe hypoalbuminemia or conditions which may interfere with implantation of peritoneal dialysis catheter, such as severe ascites, recently received abdominal surgery, abdominal mass or intestinal dilation and the likes. In addition, after long-term dialysis, peritoneum may become fibrillated, resulting in deterioration and inefficiency of peritoneal dialysis.

Problems and Complications:

Peritoneal dialysis is technically simple but highly possibly causes complications, thereby its common use is limited. Common complications of peritoneal dialysis include hypoalbuminemia and other problems such as the retention of dialysate, obstruction of dialysis catheter and peritonitis, thus the overall survival rate is only 22% (Crisp M S, Chew D J, DiBartola S P, Birchard S J. "*Peritoneal Dialysis in Dogs and Cats: 27 Cases*" (1976-1987), *J. Am. Vet. Med. Assoc.*, 195: 1262-1266, 1989). In addition, Beckel et. al. (Beckel N F, Toole T E, Rozanski E A, Labato M A. "*Peritoneal Dialysis in the Management of Acute Renal Failure in 5 Dogs with Leptospirosis*", *J. Vet. Emerg. Crit. Care*, 15:201-205, 2005) reports that peritoneal dialysis in 6 dogs with Leptospirosis shows that the subjects of about 60% take place complications including hypokalemia.

B. Hemodialysis (HD)

Principles and Methods:

Hemodialysis is in principle similar to peritoneal dialysis, however dialysis catheter (hemodialyzer) is the place where solutes are exchanged instead of peritoneum. Its methodology comprises direct exchange of blood with the dialysis solution by extracorporeal circulation, and in order to prevent the solutes from balance during hemodialysis, the blood and dialysis solution shall be continuously refreshed to maintain a concentration gradient thereby to reach a maximum diffusion.

Timing and Indications:

The indications of hemodialysis in dogs and cats mainly are ARF and its complications, acute poisoning and excessive body fluids and so on. In addition, hemodialysis is useful for acute rejection after kidney transplant until the critical conditions are eliminated.

Complications:

Hemodialysis is a technically complicated process and can be applied to physiologically and metabolically disordered patients. Common complications include catheter malfunction or catheter-related infection, low blood pressure, neurologic complications, respiratory complications, panleukopenia and thrombocytopenia, anemia, and amino acid loss. In addition, due to the complexity of the dialysis process per se and the complications of renal failure, the complications of hemodialysis adversely affect various outside kidney systems, therefore it is not easy to determine whether the adverse effects are caused by dialysis therapy itself or uremia, however the frequency and intensity of those adverse effects are generally decreased when the animals are adapted to dialysis or the uremic clearance is under control. (Cowgill L D, Langston C E. "*Role of Hemodialysis in the Management of Dogs and Cats with Renal Failure*", *Vet. Clin North. Am. Small Anim. Pract.*, 26: 1347-1378, 1996)

The mortality rate of traditional therapies for renal failure in pets are still high, and the efficiency and cost of peritoneal dialysis and/or hemodialysis therapy still need to be improved, thus there still needs a new treatment for renal failure in pets.

DESCRIPTION OF THE INVENTION

Figure 1:
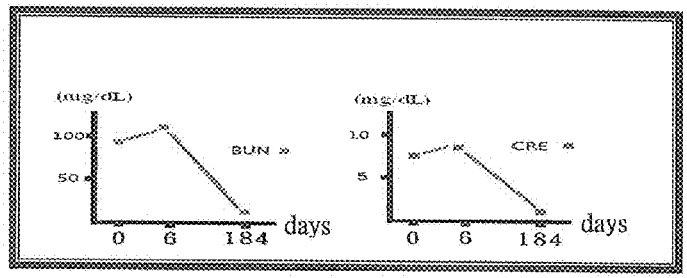
FIG. 1 shows the results of Example 1 and Table 1.

In order to overcome aforesaid drawbacks of the methods currently used for the treatment of renal failure in pets, in one embodiment, the present invention provides a novel pharmaceutical combination for treating renal failure in pets.

In another embodiment, the present invention provides a novel pharmaceutical combination for treating renal failure in pets by subcutaneous injection.

In further another embodiment, the present invention provides a novel pharmaceutical combination for treating renal failure in pets by subcutaneous injection, comprising Solution A and Solution B, wherein the Solution A and the Solution B respectively contain the following components and contents:

Solution A

| component | concentration |
| --- | --- |
| glucose | 7~42.5 g/L |
| sodium ion | 70~132 mEq/L |
| chloride ion | 45~196 mEq/L |
| calcium ion | 1.5~3.5 mEq/L |
| magnesium ion | 0.2~0.5 mEq/L |
| lactate ion | 20~40 mEq/L |

Solution B

| component | concentration |
| --- | --- |
| sodium ion | 60~130 mEq/L |
| chloride ion | 50~109 mEq/L |
| lactate ion | 15~28 mEq/L |
| potassium ion | 2.2~4 mEq/L |
| calcium ion | 1.5~3.0 mEq/L |

In a preferred embodiment, the present invention provides a pharmaceutical combination for treating renal failure in pets by subcutaneous injection, comprising Solution A and Solution B, wherein the Solution A and the Solution B respectively contain the following components and contents:

Solution A

| component | concentration |
| --- | --- |
| glucose | 7~15 g/L |
| sodium ion | 70~132 mEq/L |
| chloride ion | 45~96 mEq/L |
| calcium ion | 1.5~3.5 mEq/L |
| magnesium ion | 0.2~0.5 mEq/L |
| lactate ion | 20~40 mEq/L |

Solution B

| component | concentration |
|---|---|
| sodium ion | 60~130 mEq/L |
| chloride ion | 50~109 mEq/L |
| lactate ion | 15~28 mEq/L |
| potassium ion | 2.2~4 mEq/L |
| calcium ion | 1.5~3.0 mEq/L |

Solution A is known in the art, however it is mainly used for treating renal failure through peritoneal dialysis in abdominal cavity in order to reduce the toxin level. When Solution A is used for peritoneal dialysis in pets, however the efficiency is not quite satisfied and the pets are liable to infection with peritonitis. The inventor finds that when Solution A is administered to pets by subcutaneous injection, the exchange rate of toxins is dramatically enhanced owing to the fact that toxins are exchanged through subcutaneous tissues instead of peritoneum, and in turns the survival rate of pets is significantly improved.

Solution B is known in the art, however it is mainly applied to human or animals by vascular fluid infusion, for the purpose of supplementing body fluids lost due to burns or diarrhea, along with supplementation of electrolytes and rectification of acidosis. It has been reported that Solution B may be used in the treatment of renal failure in pets, however the efficiency is not very satisfied and a high dose is required, for example 40-60 mL/kg body weight per day, for example a dog weighing 20 kg requires fluid infusion of 800-1200 mL of Solution B per day, or a cat weighing 5 kg requires fluid infusion of 100-200 mL of Solution B twice per day. Such a high dose of infusion fluid very likely causes a serious burden on pet's body.

The inventor has conducted an intensive study and numerous clinical treatments, and found that the combination of Solution A and Solution B (hereinafter sometimes referred to as "Solution A+B") surprisingly exhibits a synergistic effect in the treatment of renal failure in animals. Specifically, the pharmaceutical combination of the present invention comprising Solution A and Solution B, when administered by subcutaneous injection, surprisingly exhibits a synergistic effect in the treatment of renal failure in animals, along with significant promotion of excretion of toxins out of the body (measured as BUN and CRE). Such synergistic effect is never suggested or taught in the prior art.

Here, the terms "combination of Solution A and Solution B" and "Solution A+B", used alternatively, do not intend to limit the manner and order of Solution A and Solution B in use. In other words, when "combination of Solution A and Solution B" or "Solution A+B" is mentioned, any one of the following conditions may be inferred: subcutaneous injection of Solution A prior to subcutaneous injection of Solution B in animals, subcutaneous injection of Solution B prior to subcutaneous injection of Solution A in animals, and direct subcutaneous injection of a mixed solution of Solution A and Solution B in animals.

In one embodiment of the present invention, the ratio of Solution A to Solution B is preferably about 1:1. However, the relative proportion of Solution A and Solution B may be adjusted by clinical veterinarians depending on the health status of animals based on their clinical experience and judgment, and is still encompassed within the scope of the invention.

Further, the inventor also found that as compared with the prior art, Solution A+B of the present invention in a very low dose can quickly excrete toxins through urine outside the body to achieve a therapeutic efficiency, without causing a serious burden on pet's body. Specifically, according to the present invention, a recommended dosage is 0.1-10 mL/kg body weight per day for Solution A and 0.1-10 mL/kg body weight for Solution B, each 1-3 times per day. However, the actual therapeutic dose may be adjusted based on experience and judgment of veterinarians depending on the health status and body weight of animals.

In one embodiment, the dose of Solution A and Solution B each generally starts at a lower level and then is gradually increased based on the experience and judgment of veterinarians depending on the health status of pets. For example, the dose of Solution A and Solution B each initially is 0.1-5 mL/kg body weight, 1-3 times per day for about 1-3 days. After the pet is adapted to the drug, the dose for injection is slowly increased (e.g., 5-10 mL/kg of body weight, 1-3 times per day) for a period of time, until the pet reaches a recovery rate of 50-90% or more (the recovery rate is varied with the age and health status of individual animal). If a continuous care treatment is required, the dose may be further decreased to 0.1-5 mL/kg body weight, 1-3 times per day, depending on the health status. In some cases of large dogs, the dose of Solution A+B for the continuous care treatment can be even decreased to, for example, 75 mL/32 kg body weight (about 2.3 mL/kg body weight) per day.

In addition, the dose of the pharmaceutical combination of the present invention may need to be modified in accordance with the body weight of animals to be treated. The dose for heavier animals (weighing more than 5 kg) is calculated in a different way. Specifically, animals weighing more than 5 kg are preferably administered at a dose of about 50-70% of the original dose calculated as mentioned above. For example, for an animal weighing 20 kg, the original dose is 20 kg×10 mL/kg=200 mL, thus the preferred dose for injection is ranging from 100 mL (=200 mL×50%) to 140 mL (=200 mL×70%). In other words, for a 20-kg animal, solution A and solution B are each administered by subcutaneous injection with a dose of approximately 100-140 mL for about 1-10 days, and then the dose may be further reduced after the animal restores its health. Therefore, the dose of the pharmaceutical combinations of the present invention is much lower than the conventional dose of Solution B as mentioned above. For example, the conventional dose of Solution B is 40-60 mL/kg body weight per day, namely 800-1200 mL for a 20-kg pet, such a high infusion dose will impart a serious load to the body and cause subcutaneous injury.

The pharmaceutical combination of the present invention is administered by subcutaneous injection to the pets in order to improve or treat renal failure, thereby it is different from traditional fluid infusion therapy, peritoneal dialysis and hemodialysis, with respect to the route of administration and the therapeutic mechanism.

The term "renal failure" herein is meant by renal failure defined and determined by the criteria known to people of ordinary skill in the art, including, for example, acute renal failure and chronic renal failure, or prerenal renal failure and intrinsic renal failure (see, for example, Liu, Chia-Yuan, "*The study of short-term prognostic factors in canine and feline renal failure*", National Taiwan University, master thesis, 2005; Tsai, Han-Ju, "*The Evaluation of Hemodialysis on Dogs with Renal Failure*", Taiwan Vet J., 29:353-358, 2003; Lin, Kai-Wei, "*Prognostic Indicators Affecting the Outcome of Acute Renal Failure in Small Animals and Evaluation of Related Infection by Using Central Venous Catheter in Dogs*", National Chung Hsing University, master thesis, 2007). In one embodiment, the pharmaceutical combination of the present invention is preferably useful in the treatment of acute renal failure and chronic renal failure.

In another embodiment, the pharmaceutical combination of the present invention is useful in the emergent rescue of acute renal failure, in the treatment of acute poisoning, and in the life-sustaining continuous care treatment of chronic renal failure in dogs and cats.

Herein, the term "emergent rescue" is meant by emergent treating behaviors conducted on a pet with renal failure who is requested for peritoneal dialysis or hemo dialysis or even is advised to give euthanasia by veterinarians after the pet is ineffective to any forms of treatment or does not receive any treatments. The purpose of emergent rescue is to maintain pet's life, prevent from progression of renal failure, and promote healing and so on.

The criteria to determine pet renal failure are generally based on blood gas level, hemobiological indices and blood electrolyte levels (such as sodium, potassium, chloride). Typically, acute renal failure and chronic renal failure are determined by BUN and CRE values. For healthy dogs and cats, normal BUN values are respectively 6-33 mg/dL and 12-41 mg/dL, and normal CRE values are respectively 0.6-1.6 mg/dL and 0.7-2.5 mg/dL. With reference to the standards for classification of renal failure in dogs and cats established by International Renal Internal Society (IRIS), based on the CRE concentration, the pet is diagnosed as end-stage or acute renal failure when the CRE value is 5 mg/dL or more. Thus, the therapeutic index or renal failure index is meant by BUN and CRE values in the present invention. In one embodiment of the present invention, the improvement and/or treatment of renal failure means that the therapeutic index or renal failure index is decreased to close to or within the normal range after being treated with the pharmaceutical combinations of the present invention.

In some cases, the BUN and/or CRE values of a pet with renal failure do not increase rapidly, but its physical conditions apparently become worse. Therefore, the status of a pet with renal failure is additionally evaluated by observation of its appearance and activity. The symptoms for diagnosis of acute renal failure generally include, for example, fatigue, drowsiness, depression, weakness, loss of appetite, dehydration, vomiting and diarrhea, as well as less common symptoms including seizures, syncope and ataxia, and the likes. Thus, in another embodiment of the present invention, improvement and/or treatment of renal failure means that aforesaid symptoms are mitigated and/or eliminated after being treated with the pharmaceutical combinations of the present invention.

In one embodiment of the present invention, the renal failure index is significantly reduced, and preferably decreased to the normal range after being treated with the pharmaceutical combinations of the present invention. Specifically, BUN and/or CRE values are significantly decreased to close to or within the normal range. In another embodiment, the renal failure index can be significantly decreased in 1-10 days, and preferably decreased to close to or within the normal range. In another embodiment, the morality rate of dogs and cats with renal failure can be significantly decreased, for example, to about 15-25% in young dogs and cats. In another embodiment, pets with renal failure are recovered in 1-10 days from initially inactive, vomiting, drowsy and convulsive conditions to active, not vomiting and motility-improved conditions, without other uncomfortable changes, and gradually return to normal physical conditions. In another embodiment, the pharmaceutical combination for the treatment of renal failure in pet according to the present invention provides a recovery rate of 50-90% or more, preferably a recovery rate of 60-90% or more, and the younger the animals are, the higher the recovery rate is. Therefore, the pharmaceutical combination of the present invention provides a significantly improved effect in the treatment of renal failure, as compared with traditional therapies (fluid infusion, peritoneal dialysis or hemodialysis) which lead to a yearly morality rate of 81.2% and 65.2% in dogs and cats respectively (i.e., a survival rate of 18.8% and 34.8% respectively).

For a pet with end-stage renal failure (where therapeutic index can not be decreased further), veterinarians generally advise peritoneal dialysis or hemodialysis or even recommend euthanasia. In the case that a pet with irreversible serious renal failure requires peritoneal dialysis for emergent rescue, the pet may need peritoneal dialysis 8-12 times per day, however its physical condition may be still getting worse and even dying. Normally, a pet may be given peritoneal dialysis about 2-5 times per day. If a pet requires peritoneal dialysis many more times per day, it implies that the exchange rate trough peritoneum of the pet to be treated is no longer efficient and can not be recovered, thereby euthanasia may be recommended. In another embodiment, when emergent rescue is conducted on a pet with renal failure with the pharmaceutical combination of the present invention, the recovery rate (of emergent rescue for 1-10 days) is 60-90% or more in young dogs and cats (0-6 years) and about 50-60% in old dogs and cats (7 years or more), thus the overall recovery rate is 50-90% or more in dogs and cats.

In further another embodiment, the pharmaceutical combination of the present invention provides a significantly increased recovery rate in the continuous care treatment of pets with renal failure. To date, no specific methods are available in the continuous care treatment for both reversible and irreversible forms of renal failure. Pets with reversible renal failure may remain stable after peritoneal dialysis or hemodialysis therapy is removed. However, the continuous care treatment becomes a serious problem in the case of irreversible renal failure, since the renal failure index generally rise again after removal of catheter for peritoneal dialysis or hemodialysis even the pets is stable before. Therefore, in another embodiment, the pharmaceutical combination of the present invention is useful in the continuous care treatment, in addition to the treatment of renal failure in pets. As long as no other deterioration factors causing death, after recovered well through treating with the pharmaceutical combination of the present invention, the pet with renal failure may be continuously administered with the pharmaceutical combination of the present invention for the continuous care treatment. Therefore, the pharmaceutical combination of the present invention is useful for the continuous care treatment of pets with renal failure, thereby providing a much enhanced outcome.

Therefore, the pharmaceutical combination for the treatment of renal failure by subcutaneous injection in pets according to the present invention has the following advantages:

(1) The pharmaceutical combination for the treatment of renal failure according to the present invention is different from the methods currently used in the art for the treatment of renal failure with respect to the route of administration and therapeutic mechanisms, and has a significantly improved efficiency in the removal of toxins (measured as BUN and CRE), thereby the toxin level in pet's body can be more rapidly reduced, so that the pets can quickly restore and maintain health.

(2) For a pet at the end stage of renal failure, when the therapeutic indices continuously rise even after traditional therapy and peritoneal dialysis or hemodialysis, it means that maintaining pet life is difficult, then veterinarians usually recommend palliative care (or euthanasia). The present invention provides a pharmaceutical combination which is effective in life-sustaining care for pets for whom other therapies are ineffective or euthanasia is requested.

(3) The pharmaceutical combination for the treatment of renal failure according to the present invention is useful in the treatment of in-hospital determined acute renal failure or chronic renal failure in pets.

(4) The pharmaceutical combination of the present invention improves the recovery rate of renal failure by 60-90% or more (about 50-60% for animals of 7 years or older), and can be continuously used to perform the continuous care treatment.

(5) The present invention provides a pharmaceutical combination which is simple and convenient in the treatment of renal failure, and thus can be used to perform continuous care treatment by pet owner at home after the pet is discharged from the hospital, thereby the recovery rate can be further improved.

(6) The pharmaceutical combination of the present invention is administered by subcutaneous injection, and does not require surgery, hospitalization, or intravenous infusion. Infections can be reduced and free movement is allowed. Thereby, pets with renal failure can be treated in a humanistic way and live with dignity, with a prolonged life.

(7) The dose of the pharmaceutical combination of the present invention for subcutaneous injection (0.1-10 mL/kg body weight) is much lower than the dose conventionally used in the art for the treatment of renal failure (for example, 40-60 mL/kg body weight for Solution B).

(8) The pharmaceutical combination of the present invention has much less adverse effects. Many infections such as catheter-related infections can be avoided since no fluid infusion or dialysis is used, thus complications and infections are much less, thereby safety is relatively improved a lot.

According to the present invention, the term "recovery rate" means a proportion of the number of pets with renal failure who can not restore health without treatment or after antecedent treatment through fluid infusion or peritoneal dialysis or hemodialysis requested by veterinarians, and thus are treated with the pharmaceutical combination of the present invention for 1-10 days, from which the normal health status is restored back by 50-90% or more, and/or BUN and/or CRE value is significantly reduced to close to or within the normal range, and/or pet's activity is restored with no vomiting and other special uncomfortable changes, to the number of pets with renal failure under the same condition but not treated with the pharmaceutical combination of the present invention.

According to the invention, the terms "pet" and "animal" mean dogs, cats, rabbits, mice and other small animals, preferably dogs or cats.

The following examples will further describe the representative embodiments of the present invention, however these examples are intended only for illustration absolutely not for limitation of the content and scope of the present invention. People of ordinary skill in the art will understand that many modifications and variations may be made thereto in light of the above teachings to obtain the same or equivalent results, without departing from the scope of the appended claims.

EXAMPLE

Preparation

Solution A and Solution B are formulated to have the following components and contents:

Solution A containing: 15 g 1L of glucose, 132 mEq/L of sodium ion, 96 mEq/L of chloride ion, 3.5 mEq/L of calcium ion, 0.5 mEq/L of magnesium ion, and 40 mEq/L of lactate ion.

Solution B containing: 130 mEq/L of sodium ion, 109 mEq/L of chloride ion, 28 mEq/L of lactate ion, 4 mEq/L of potassium ion, and 3.0 mEq/L of calcium ion.

Method of Testing and Evaluation:

The effect of the pharmaceutical combination of the present invention in the treatment of renal failure in pets is evaluated by measuring BUN and CRE values and by observing the appearance and activity in pets. BUN and CRE values are measured on a biochemical analyzer (SPOTCHEM, model 4430, manufactured by Arkray Inc.). The ranges of BUN and CRE values of dogs and cats in different health status are listed as follows:

|  |  | BUN (mg/dL) | CRE (mg/dL) |
| --- | --- | --- | --- |
| dog | normal status | 6-33 | 0.6-1.6 |
| cat | normal status | 12-41 | 0.7-2.5 |
| dog/cat | renal failure | 80-100 | 8-10 |

Additionally, the health status of pets with renal failure is evaluated by observation of appearance and activity. Specifically, the effect in the treatment of renal failure is evaluated by observation of alleviation and/or elimination of symptoms including fatigue, depression, weakness, loss of appetite, dehydration, vomiting and diarrhea and the like in pets.

Procedures of Treatment:

Prior to administration, the health status of individual pets to be treated is evaluated by measuring BUN and CRE values and blood gas values, as well as by observing pets' appearance and activity. In the drug running-in period, Solution A (0.1-5 mL/kg body weight) is injected subcutaneously into one side of the back of the pet body, followed by subcutaneous injection of Solution B (0.1-5 mL/kg body weight) into the other side of the back of the pet body. In some cases, a mixed solution of Solution A and Solution B is directly administered by subcutaneous injection when the health status of the pet is allowed. (Days 1-3) The same amount of Solution A and Solution B is repetitiously administered by subcutaneous injection every 8-12 hours (i.e., 2-3 times per day), with periodic measurement of BUN and CRE values and observation of pet's appearance and activity. (Days 4-10) When the pet is acceptable to the running-in drug, the amount of Solution A and Solution B is gradually increased to 5-10 mL/kg body weight (1-3 times per day). If the pet is detoxified at the drug running-in period (namely, Days 1-10, called prime time of rescue) and the pet's health is restored by 50-90% or more (the recovery rate of individual animals is varied with age and health status), the amount of injection can be reduced to less than 10 mL/kg body weight. If the pet recovers well and looks good in activity and movement in 7-10 days, a mixed solution of Solution A and Solution B may be directly subcutaneously injected. The extension of days for injection or reduction of the dose may be adjusted individually depending on the health status of the pet.

Example 1

Dog

Basic information: breed variety: Maltese; gender: female; age: 14 years old; body weight: 4 kg.

Animal health status before injection (day 0): the animal was diagnosed as acute renal failure due to inappropriate steroid treatment and its health was deteriorated rapidly.

Medical treatment and method: Solution A and Solution B each were administered by subcutaneous injection to each side of the back of the animal, and then (starting at day 3) Solution A+B (a mixed solution of Solution A and Solution B) was directly injected subcutaneously, with the dose being gradually reduced.

The result of the treatment by the pharmaceutical combination of the present invention is shown in Table 1 and FIG. 1.

TABLE 1

|  | day | | |
| --- | --- | --- | --- |
|  | day 0 | day 6 | day 184 |
| appearance | lethargic, inactive, vomiting | normal, active | normal, active |
| BUN (mg/dL) | 92 | 117 | 17 |
| CRE (mg/dL) | 7.9 | 8.4 | 1.1 |

Example 2

Dog

Basic information: breed variety: hybrid; gender: female; age: 6 years old; body weight: 18 kg.

Animal health status before injection (day 0): the animal was diagnosed as acute renal failure due to inappropriate steroid treatment and its health was deteriorated rapidly.

Medical treatment and method: direct subcutaneous injection of Solution A+B.

Figure 2:
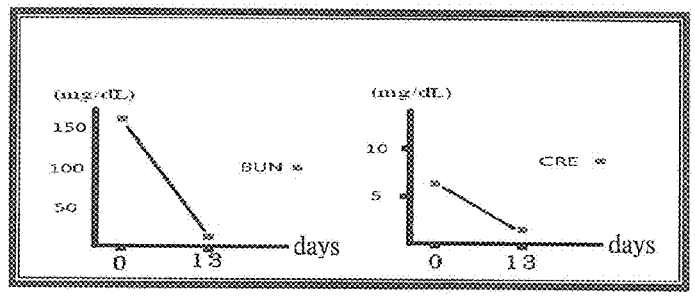
FIG. 2 shows the results of Example 2 and Table 2.

The result of the treatment by the pharmaceutical combination of the present invention is shown in Table 2 and FIG. 2.

TABLE 2

|  | day | |
| --- | --- | --- |
|  | day 0 | day 13 |
| appearance | bad breathing, inactive, vomiting | normal, active |
| BUN (mg/dL) | 158 | 18 |
| CRE (mg/dL) | 6.7 | 1.9 |

Example 3

Dog

Basic information: breed variety: Husky; gender: male; age: 5 years old; body weight: 19.6 kg.

Animal health status before injection (day 0): the animal was antecedently treated in other hospital with fluid infusion which however was ineffective, with progression to acute renal failure, and then was requested for peritoneal dialysis or hemodialysis or euthanasia by veterinarian.

Medical treatment and method: direct subcutaneous injection of Solution A+B.

Figure 3:
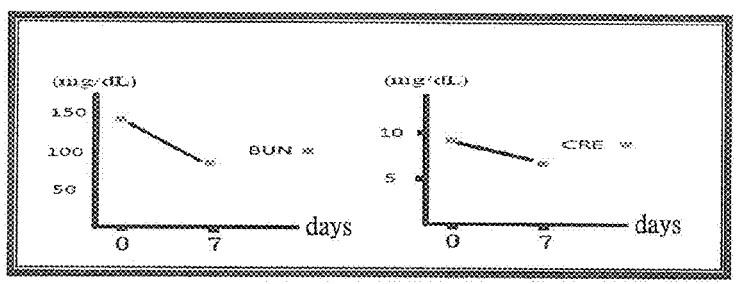
FIG. 3 shows the results of Example 3 and Table 3.

The result of the treatment by the pharmaceutical combination of the present invention is shown in Table 3 and FIG. 3.

TABLE 3

|  | day | |
| --- | --- | --- |
|  | day 0 | day 7 |
| appearance | inactive, vomiting | normal, active |
| BUN (mg/dL) | 147 | 92 |
| CRE (mg/dL) | 9.4 | 7.3 |

Example 4

Dog

Basic information: breed variety: Labrador; gender: female; age: 6 years old; body weight: 31.85 kg.

Animal health status before injection (day 0): the animal was antecedently treated in other hospital with fluid infusion and then subcutaneous injection which however were ineffective, with progression to acute renal failure, and then was requested for peritoneal dialysis or hemodialysis or euthanasia by veterinarian.

Medical treatment and method: Solution A+B was initially subcutaneously injected, and starting at day 60, only Solution A was injected and the dose was reduced to 75 mL once per day.

Figure 4:
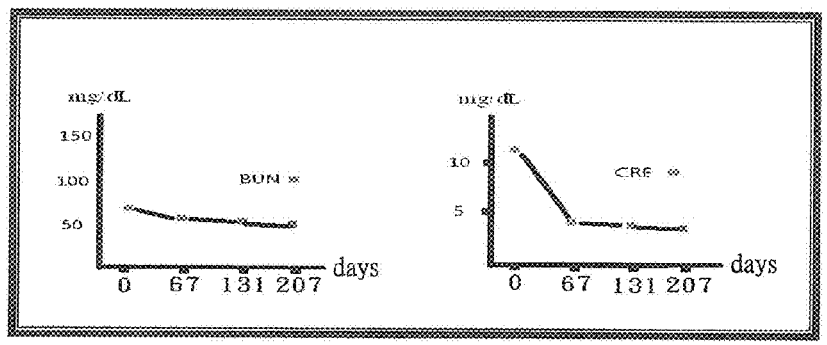
FIG. 4 shows the results of Example 4 and Table 4.

The result of the treatment by the pharmaceutical combination of the present invention is shown in Table 4 and FIG. 4.

TABLE 4

|  | day | | | |
| --- | --- | --- | --- | --- |
|  | day 0 | day 67 | day 131 | day 207 |
| appearance | inactive, vomiting | normal, active | normal, active, increasing body weight | normal, active, increasing body weight |
| BUN (mg/dL) | 77 | 63 | 60 | 52 |
| CRE (mg/dL) | 11.1 | 3.9 | 3.8 | 3.7 |

Example 5

Cat

Basic information: breed variety: hydrid; gender: male; age: 4 years old; body weight: 4.8 kg.

Animal health status before injection (day 0): the animal was antecedently treated in other hospital with fluid infusion and then subcutaneous injection with Solution B, which however were ineffective, with progression of from chronic renal failure to acute renal failure, and then was requested for peritoneal dialysis or hemodialysis or euthanasia by veterinarian.

Medical treatment and method: Solution A was initially subcutaneously injected, and then starting at day 364, Solution A+B was subcutaneously injected, with the dose being gradually reduced.

Figure 5:
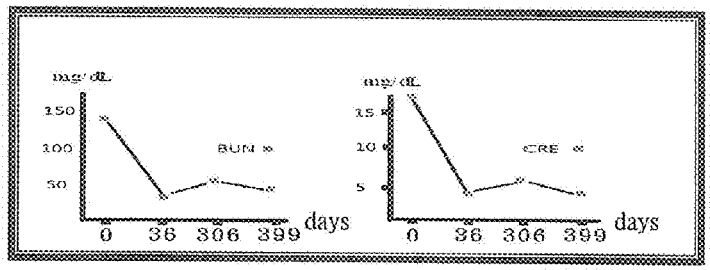
FIG. 5 shows the results of Example 5 and Table 5.

The result of the treatment by the pharmaceutical combination of the present invention is shown in Table 5 and FIG. 5.

TABLE 5

| | day | | | | |
|---|---|---|---|---|---|
| | day 0 | day 36 | day 306 | day 364 | day 399 |
| appearance | inactive | normal, active | normal, active | normal, active | normal, active |
| solution injected | A | A | A | A + B | A + B |
| BUN (mg/dL) | 140 | 36 | 60 | ND* | 46 |
| CRE (mg/dL) | 17.5 | 4.0 | 5.8 | ND* | 4.1 |

*ND: undetermined

Example 6

Cat

Figure 6:
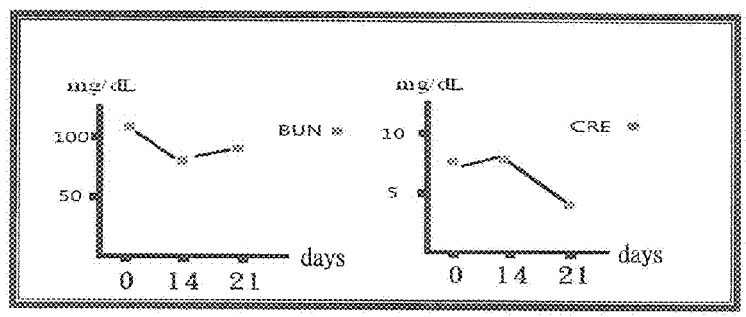
FIG. 6 shows the results of Example 6 and Table 6.

Basic information: breed variety: Persian; gender: male; age: 10 years old; body weight: 6.1 kg.
Animal health status before injection (day 0): the animal was antecedently treated in other hospital with fluid infusion and then subcutaneous injection with Solution B, which however were ineffective, with progression of from chronic renal failure to acute renal failure, and then was requested for peritoneal dialysis or hemo dialysis or euthanasia by veterinarian.
Medical treatment and method: direct subcutaneous injection of Solution A+B.
The result of the treatment by the pharmaceutical combination of the present invention is shown in Table 6 and FIG. 6.

TABLE 6

| | day | | |
|---|---|---|---|
| | day 0 | day 14 | day 21 |
| appearance | inactive | normal, active | normal, active |
| BUN (mg/dL) | 107 | 79 | 88 |
| CRE (mg/dL) | 7.8 | 7.9 | 4.6 |

Example 7

Cat

Figure 7:
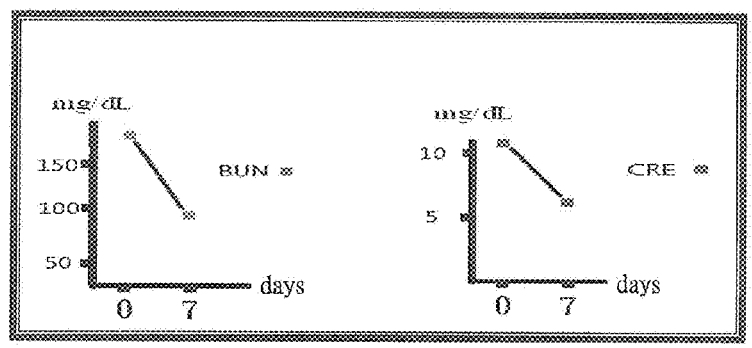
FIG. 7 shows the results of Example 7 and Table 7.

Basic information: breed variety: Persian; gender: female; age: 13 years old; body weight: 2.55 kg.
Animal health status before injection (day 0): the animal was antecedently treated in other hospital with fluid infusion which however was ineffective, with progression to acute renal failure, and then was requested for peritoneal dialysis or hemodialysis or euthanasia by veterinarian.
Medical treatment and method: direct subcutaneous injection of Solution A+B.
The result of the treatment by the pharmaceutical combination of the present invention is shown in Table 7 and FIG. 7.

TABLE 7

| | day | |
|---|---|---|
| | day 0 | day 7 |
| appearance | inactive, heavy breathing | normal |
| BUN (mg/dL) | 174 | 95 |
| CRE (mg/dL) | 10.6 | 6.8 |

Example 8

Cat

Figure 8:
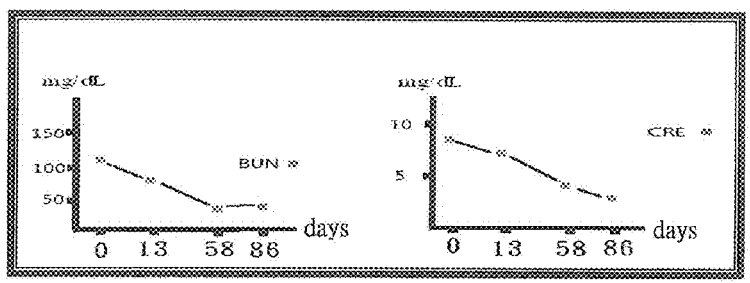
FIG. 8 shows the results of Example 8 and Table 8.

Basic information: breed variety: hydrid; gender: female; age: 3 years old; body weight: 2.9 kg.
Animal health status before injection (day 0): the animal with acute renal failure was antecedently treated in other hospital with fluid infusion which however was ineffective, and was then requested for emergent peritoneal dialysis by veterinarian.
Medical treatment and method: direct subcutaneous injection of Solution A+B, with the dose being gradually reduced.
The result of the treatment by the pharmaceutical combination of the present invention is shown in Table 8 and FIG. 8.

TABLE 8

| | day | | | |
|---|---|---|---|---|
| | day 0 | day 13 | day 58 | day 86 |
| appearance | inactive | normal | normal | normal |
| BUN (mg/dL) | 113 | 89 | 34 | 41 |
| CRE (mg/dL) | 8.7 | 7.4 | 4.6 | 3.5 |

Example 9

Cat

Figure 9:
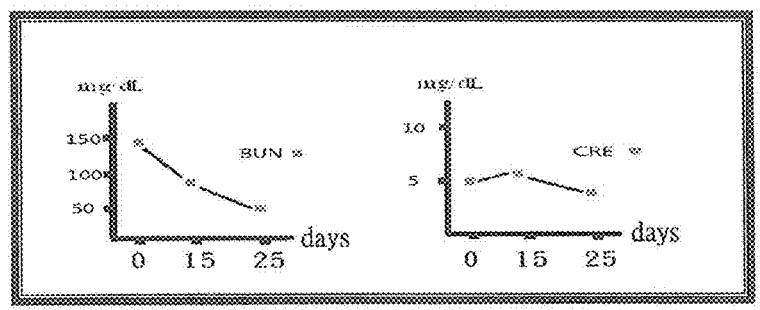
FIG. 9 shows the results of Example 9 and Table 9.

Basic information: breed variety: hybrid; gender: female; age: 3 years old; body weight: 2.6 kg.
Animal health status before injection (day 0): the animal with acute renal failure was antecedently treated in other hospital with peritoneal dialysis which however was ineffective, and then was requested for peritoneal dialysis or hemodialysis or euthanasia by veterinarian.
Medical treatment and method: direct subcutaneous injection of Solution A+B.
The result of the treatment by the pharmaceutical combination of the present invention is shown in Table 9 and FIG. 9.

TABLE 9

| | day | | |
|---|---|---|---|
| | day 0 | day 15 | day 25 |
| appearance | inactive, uncomfortable | normal | normal |
| BUN (mg/dL) | 149 | 82 | 50 |
| CRE (mg/dL) | 5.0 | 5.8 | 4.0 |

Example 10

Cat

Figure 10:
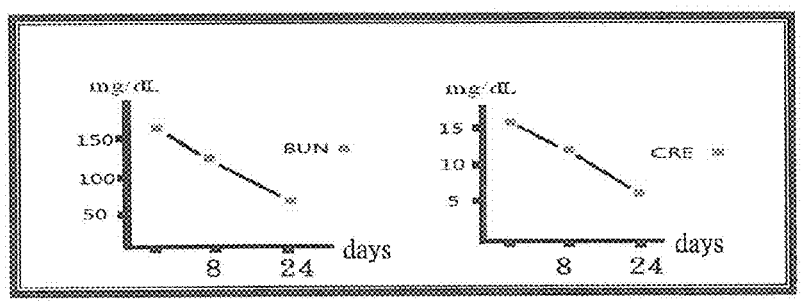
FIG. 10 shows the results of Example 10 and Table 10.

Basic information: breed variety: American Shorthair; gender: male; age: 4 years old; body weight: 3.35 kg.
Animal health status before injection (day 0): the animal was antecedently treated in other hospital with peritoneal dialysis which however was ineffective, with progression of from chronic renal failure to acute renal failure.
Medical treatment and method: direct subcutaneous injection of Solution A+B followed by subcutaneous injection of the same solution but in a gradually reduced dose.
The result of the treatment by the pharmaceutical combination of the present invention is shown in Table 10 and FIG. 10.

TABLE 10

| | day | | |
|---|---|---|---|
| | day 0 | day 8 | day 24 |
| appearance | inactive, vomiting | normal, active, trying to pull out catheter | normal, active |
| BUN (mg/dL) | 156 | 126 | 60 |
| CRE (mg/dL) | 15.6 | 6.7 | 5.8 |

Example 11

Cat

Basic information: breed variety: Himalayan; gender: male; age: 16 years old; body weight: 2.35 kg.
Animal health status before injection (day 0): the animal was diagnosed as acute renal failure without any treatment, and looked very uncomfortable.
Medical treatment and method: direct subcutaneous injection of Solution A+B.

Figure 11:
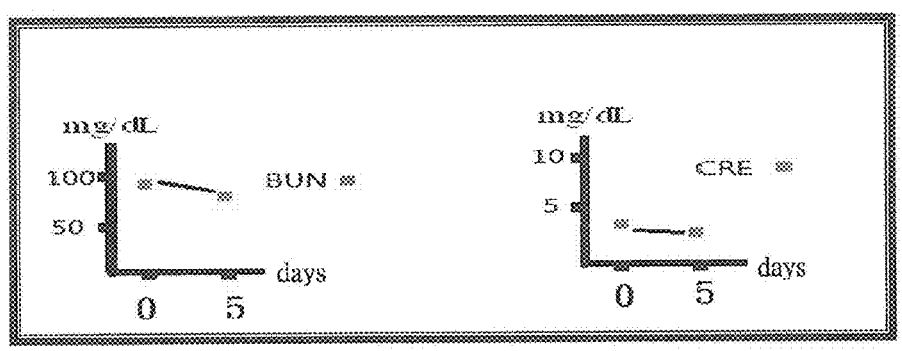
FIG. 11 shows the results of Example 11 and Table 11.

The result of the treatment by the pharmaceutical combination of the present invention is shown in Table 11 and FIG. 11.

TABLE 11

| | day | | |
|---|---|---|---|
| | day 0 | day 5 | day 8 |
| appearance | inactive, lethargic | gradually normal but still weak | improved activity, good appetite and running |
| BUN (mg/dL) | 99 | 89 | ND* |
| CRE (mg/dL) | 3.7 | 3.2 | ND* |

*ND: undetermined

What is claimed is:

1. A method for treating renal failure in pets comprising injecting subcutaneously, to a pet in need thereof, a combination of Solution A and Solution B, wherein the relative proportion of the Solution A to the Solution B is 1:1, and the Solution A and the Solution B contain the following components and contents:

Solution A

| Component | concentration |
|---|---|
| glucose | 7~15 g/L |
| sodium ion | 70~132 mEq/L |
| chloride ion | 45~96 mEq/L |
| calcium ion | 1.5~3.5 mEq/L |
| magnesium ion | 0.2~0.5 mEq/L |
| lactate ion | 20~40 mEq/L |

Solution B

| Component | concentration |
|---|---|
| sodium ion | 60~130 mEq/L |
| chloride ion | 50~109 mEq/L |
| lactate ion | 15~28 mEq/L |
| potassium ion | 2.2~4 mEq/L |
| calcium ion | 1.5~3.0 mEq/L. |

2. The method of claim 1, wherein the Solution A and the Solution B contain the following components and contents:

Solution A

| component | Concentration |
|---|---|
| glucose | 7~15 g/L |
| sodium ion | 70~132 mEq/L |
| chloride ion | 45~96 mEq/L |
| calcium ion | 1.5~3.5 mEq/L |
| magnesium ion | 0.2~0.5 mEq/L |
| lactate ion | 20~40 mEq/L |

Solution B

| component | Concentration |
|---|---|
| sodium ion | 60~130 mEq/L |
| chloride ion | 50~109 mEq/L |
| lactate ion | 15~28 mEq/L |
| potassium ion | 2.2~4 mEq/L |
| calcium ion | 1.5~3.0 mEq/L. |

3. The method of claim 1, wherein the renal failure includes renal failure caused by various diseases.

4. The method of claim 1, wherein the treatment of renal failure includes the emergent rescue of renal failure.

5. The method of claim 1, wherein the treatment of renal failure includes the continuous care treatment of renal failure.

6. The method of claim 1, wherein the Solution A and the Solution B each is administered in an amount of 0.1-10 mL/kg body weight, 1 to 3 times per day.

* * * * *